| United States Patent [19] | [11] 4,012,528 |
|---|---|
| Jen et al. | [45] Mar. 15, 1977 |

[54] α-AMINOALKYL-3-(1,2-DIHYDROXYETHYL)-4-HYDROXY-BENZYL ALCOHOLS HAVING β-ADRENERGIC STIMULANT ACTIVITY

[75] Inventors: Timothy Yu-Wen Jen, Broomall, Pa.; Carl Kaiser, Haddon Heights; Joe R. Wardell, Willingboro, both of N.J.

[73] Assignee: SmithKline Corporation, Philadelphia, Pa.

[22] Filed: June 13, 1975

[21] Appl. No.: 586,828

Related U.S. Application Data

[63] Continuation-in-part of Ser. No. 475,675, June 3, 1974, abandoned.

[30] Foreign Application Priority Data

May 5, 1975 United Kingdom ............ 18669/75

[52] U.S. Cl. .................... 424/330; 260/340.5; 260/570.5 R; 260/570.5 CA; 260/570.7; 424/45; 424/282

[51] Int. Cl.² .................... A61K 31/135
[58] Field of Search .................... 424/282, 330; 260/340.5, 570.5 R, 570.5 CA, 570.7

[56] References Cited

UNITED STATES PATENTS

| 3,705,233 | 12/1972 | Lunts et al. | 424/330 X |
| 3,732,300 | 5/1973 | Lunts et al. | 424/330 X |

Primary Examiner—Albert T. Meyers
Assistant Examiner—Vera C. Clarke
Attorney, Agent, or Firm—Richard D. Foggio; William H. Edgerton

[57] ABSTRACT

α-Aminoalkyl-3-(1,2-dihydroxyethyl)-4-hydroxy-benzyl alcohols having β-adrenergic stimulant activity, particularly as selective bronchodilators, are disclosed.

19 Claims, No Drawings

α-AMINOALKYL-3-(1,2-DIHYDROXYETHYL)-4-HYDROXY-BENZYL ALCOHOLS HAVING β-ADRENERGIC STIMULANT ACTIVITY

This application is a continuation-in-part of application Ser. No. 475,675 filed June 3, 1974, now abandoned.

This invention relates to novel α-aminoalkyl-3-(1,2-dihydroxyethyl)-4-hydroxy-benzyl alcohols which have useful pharmacodynamic activity. More specifically, the compounds of this invention have utility as β-adrenergic stimulants with relatively greater activity on respiratory smooth muscle than on cardiac muscle. Therefore these compounds have direct bronchodilator action with minimal cardiac stimulation as demonstrated in standard pharmacological test procedures.

Two in vitro test systems used for determining selective β-stimulant activity are: (1) effect on spontaneous tone of guinea pig tracheal chain preparations as a measure of β-stimulant (direct relaxant) effect on airway smooth muscle, and (2) effect on rate of spontaneously beating right atria of the guinea pig as a measure of β-stimulant effect on cardiac muscle. The compounds of this invention have selective bronchodilating properties since they are active in (1) above at a dose lower than is required in (2) above resulting in a positive separation ratio.

The compounds of this invention are represented by the following general structural formula:

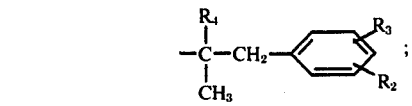

FORMULA I in which:

R represents hydrogen or methyl, with both R's not being methyl at the same time;

$R_1$ represents a branched chain lower alkyl group of from 3 to 5 carbon atoms, a cycloalkyl or cycloalkyl methyl group, the cycloalkyl moiety having from 3 to 6 carbon atoms, or

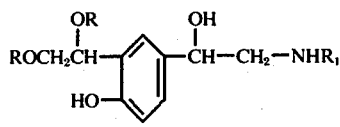

$R_2$ and $R_3$ represent hydrogen, hydroxy, methoxy, or taken together in adjacent positions, methylenedioxy; and $R_4$ represents hydrogen or methyl.

Preferred compounds of this invention are represented by formula I above when R is hydrogen and $R_1$ is isopropyl, t-butyl, cyclopropyl, cyclopentyl, 4-hydroxyphenylisopropyl, 3,4-methylenedioxyphenylisopropyl or 3,4-dimethoxyphenylisopropyl.

The compounds of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bis-methylenesalicylic, methanesulfonic, ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexyl sulfamic, phosphoric and nitric acids.

Further the compounds of this invention contain two asymmetric carbon atoms and may be present as diastereoisomers, each of which may be resolved as d and l-optical isomers. Unless otherwise specified in the description and accompanying claims, it is intended to include all isomers, whether separated or mixtures thereof.

A preferred compound of this invention is α-(t-butylaminomethyl)-3-(1,2-dihydroxyethyl)-4-hydroxybenzyl alcohol which relaxes the spontaneous tone of guinea pig tracheal ring preparation at an $ED_{50}$ of 0.018 mcg/ml while increasing the rate of contraction of guinea pig right atria at an $ED_{25}$ of 1.9 mcg/ml. These activities give an absolute separation ratio of 105 which is a 210 fold improvement when compared to the corresponding activity of d, 1-isoproterenol (absolute separation ratio = 0.5) in similar in vitro preparations.

The compounds of this invention where R is hydrogen are prepared as shown in the following sequence of reactions:

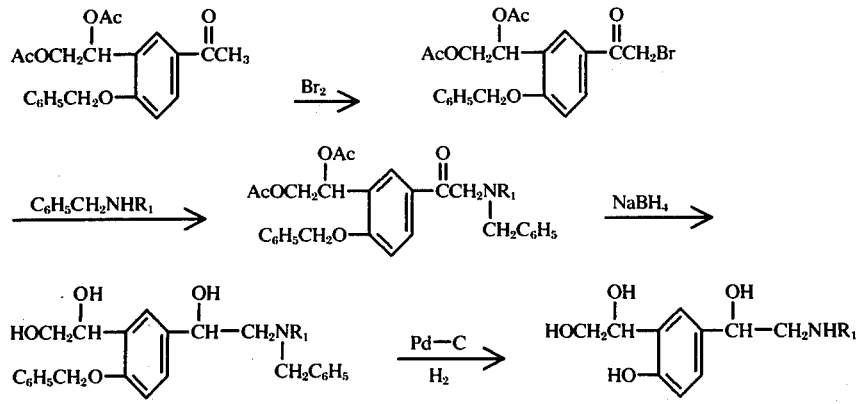

in which Ac is acetyl and $R_1$ is as defined in formula I. Thus, as shown above, an appropriately protected acetophenone is treated with bromine or pyrrolidone hydrotribromide to give the α-bromoacetophenone. The latter is reacted with an N-benzylamine and the resultant α-benzylaminoacetophenone is treated with sodium borohydride to give the corresponding benzyl alcohol intermediate. This compound is hydrogenated catalytically, preferably with palladium-on-carbon, to give the debenzylated dihydroxyethyl benzyl alcohol product.

Similarly, to prepare the compounds of this invention where R is methyl, the analogous 1-methoxy-2-acetoxy or 1-acetoxy-2-methoxy acetophenone is used as the starting material in the above sequence of reactions.

It will be appreciated that the benzylated derivatives of the following formula:

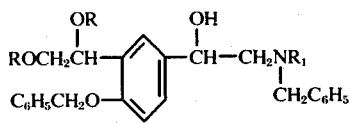

in which R and R₁ are as defined in formula I, are useful intermediates in the preparation of the products of this invention and as such form a part of the invention.

The protected acetophenones used as starting materials herein are prepared by methods known in the art. For example, methyl salicylate is treated with acetyl chloride under Friedel-Crafts reaction conditions to yield methyl 5-acetylsalicylate which is reacted with benzyl chloride in the presence of potassium hydroxide or potassium carbonate to give the corresponding benzyl ether. The latter is treated with ethylene glycol and p-toluenesulfonic acid, followed by reduction of the resultant 1,3-dioxolane, with lithium aluminum hydride to the salicyl alcohol. This derivative is oxidized to a benzaldehyde using manganese dioxide which is then treated with trimethylsulfonium iodide and sodium hydride in dimethylsulfoxide to convert the aldehyde group to an epoxide. Treatment of the epoxide with perchloric acid in dioxane yields 4-benzyloxy-3-(1,2-dihydroxyethyl)-acetophenone; acid catalyzed methanolysis of the epoxide gives the 3-(2-hydroxy-1-methoxyethyl)acetophenone; and treatment of the epoxide with sodium methoxide-methanol gives a mixture of primary and secondary alcohols which is separated to give the 3-(1-hydroxy-2-methoxyethyl)acetophenone. Subsequent acetylation in pyridine furnishes the required acetylated acetophenones.

U.S. Pat. No. 3,644,353 describes α-aminoalkyl-4-hydroxy-3-(hydroxyalkyl)-benzyl alcohols, however, there is no disclosure of the 3-(1,2-dihydroxyethyl)-benzyl alcohols of this invention. In addition to structural features, the compounds of this invention are further distinguished by having marked separation between bronchodilator action and cardiac stimulation.

The compounds of this invention may be administered orally or parenterally in conventional dosage unit forms such as tablets, capsules, injectables, aerosols, or the like, by incorporating the appropriate dose of a compound of formula I with carriers according to accepted pharmaceutical practices.

Preferably a compound or an acid addition salt thereof is administered orally to an animal organism in a tablet or capsule comprising an amount sufficient to produce β-adrenergic stimulant activity. Each dosage until will contain the active ingredient in an amount of about 10 mg. to about 500 mg., preferably from about 20 mg. to about 300 mg. Advantageously equal doses will be administered 2 to 4 times daily with the daily dosage regimen being about 20 mg. to about 2000 mg., preferably from about 40 mg. to about 1200 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampule, or an aqueous or nonaqueous liquid suspension.

Of particular applicability is an aerosol dispensing system wherein the active medicament is incorporated with Freon (fluorohydrocarbon) or other inert propellant in an aerosol container. Such an aerosol system will deliver a metered dose of about 100 mcg. to about 1000 mcg. administered once or twice at a time as needed.

The foregoing is a general description of how to prepare the compounds of this invention. The following examples illustrate the preparation of specific compounds having β-adrenergic stimulant activity. However, this should not be construed as a limitation of the invention since appropriate variations in the starting materials will produce other products set forth hereinabove.

PREPARATION OF
4-BENZYLOXY-3-(1,2-DIACETOXYETHYL-)ACETOPHENONE

A solution of 75 g. (0.5 m.) of methyl salicylate in 200 ml. of tetrachloroethylene is cooled in an ice bath and treated with a solution of 40 g. (0.5 m.) of acetyl chloride in 200 ml. of tetrachloroethylene. To the chilled mixture is added 133 g. (1.0 m.) of aluminum chloride over a fifteen minute period, maintaining the temperature below 25° C. After the adddition is completed the mixture is stirred for 4 hours at 25° C. and then poured into ice water. The organic layer is separated, washed with water and saturated aqueous sodium bicarbonate solution, dried and evaporated. The residual oil is crystallized from hexane to give methyl 5-acetylsalicylate, m.p. 60°–62° C.

A mixture of 54 g. (0.278 m.) of methyl 5-acetylsalicylate, 33.4 ml. (0.292 m.) of benzyl chloride, 40.3 g. (0.292 m.) of potassium carbonate and 3 g. of sodium iodide in 750 ml. of acetone is stirred and heated at reflux overnight. The reaction mixture is cooled, filtered and the solvent evaporated. The residue is dissolved in ethyl acetate, washed with water, dried and concentrated to a small volume. Addition of hexane and chilling yields the benzyl ether of methyl 5-acetyl-salicylate, m.p. 68°–70° C.

The benzyl ether (54 g., 0.19 m.), 25 ml. of ethyleneglycol and 2.0 g. of p-toluenesulfonic acid in 500 ml. of benzene are refluxed overnight, with the water being removed with a Dean-Stark trap. The cooled reaction mixture is washed with 5% aqueous sodium carbonate solution, then water and dried. Evaporation of the benzene gives the 1,3-dioxolane derivative as an oil. A solution of the latter in 300 ml. of ether is slowly added to a stirred suspension of 7.0 g. of lithium aluminum hydride in 500 ml. of ether. The mixture is refluxed for two hours and stirred overnight at 24° C. Excess lithium aluminum hydride is destroyed with 14 ml. of water and 11.5 ml. of 10% aqueous sodium hydroxide solution. This mixture is filtered and the ether evaporated to give 2-(4-benzyloxy-3-hydroxymethylphenyl)-2-methyl-1,3-dioxolane as an oil.

A solution of the 1,3-dioxolane thus prepared (13.5 g., 0.045 m.) in 350 ml. of methylene chloride is stirred for one hour with 100 g. of activated manganese dioxide. The reaction mixture is filtered, the filter cake washed well with methylene chloride and the filtrate evaporated to yield 2-(4-benzyloxy-3-formylphenyl)-2-methyl-1,3-dioxolane, m.p. 78°–80° C.

A suspension of 2.42 g. (50.4 mm.) of sodium hydride (50% dispersion washed free of mineral oil) in 35 ml. of dry dimethylsulfoxide is heated to 65° C. under argon for 1 hour. The oil bath is removed and to the clear solution is added 50 ml. of dry tetrahydrofuran. The solution is cooled to −15° C. and treated with a solution of 9.46 g. (46.4 mm.) of trimethylsulfonium iodide in 50 ml. of dry dimethylsulfoxide. After three minutes a solution of 13.8 g. (46.4 mm.) of 2-(4-benzyloxy-3-formylphenyl)-2-methyl-1,3-dioxolane in 75 ml. of tetrahydrofuran is added. The resulting mixture is allowed to cool to ambient temperature with stirring and then stirred overnight. The reaction mixture is poured into water and extracted with ether. The extracts are washed with water, dried and evaporated to give 2-[4-benzyloxy-3-(1,2-epoxyethyl)-phenyl]-2-methyl-1,3-dioxolane as an oil.

To a solution of this 1,3-dioxolane (8.8 g., 0.028 m.) in a mixture of 100 ml. of dioxane and 20 ml. of water is added, at 24° C., 1.5 ml. of perchloric acid. After 15 minutes the acid is neutralized with 5% aqueous sodium carbonate solution and the solvent is evaporated. The residue is taken up in ethyl acetate, washed with water, dried and evaporated to yield 4-benzyloxy3-(1,2-dihydroxyethyl)-acetophenone, m.p. 121°–123° C.

A solution of the acetophenone (7.2 g., 0.025 m.) in a mixture of 40 ml. of pyridine and 15 ml. of acetic anhydride is stirred overnight at 24° C. Excess acetic anhydride is decomposed by adding 10 ml. of methanol to the chilled reaction mixture and stirred for 30 minutes. The mixture is poured into water and extracted with ether. The extracts are washed well with dilute hydrochloric acid, water and dried. Evaporation of the ether furnishes 4-benzyloxy-3-(1,2-diacetoxyethyl)acetophenone as an oil.

EXAMPLE 1

To a stirred solution of 8.9 g. (0.024 m.) of 4-benzyloxy-3-(1,2-diacetoxyethyl)acetophenone in 250 ml. of tetrahydrofuran is added 1.82 ml. of 2-pyrrolidone and 11.93 g. (0.024 m.) of pyrrolidone hydrotribromide. The mixture is refluxed for 2½ hours, filtered and the filtrate concentrated. Addition of water precipitates an oil which is dissolved in ether, washed with water, dried and evaporated to yield α-bromo-4-benzyloxy-3-(1,2-diacetoxyethyl)acetophenone, m.p. 79.5°–82° C.

A solution of 4.4 g. (9.8 mm.) of the α-bromoacetophenone and 3.04 g. (18.6 mm.) of N-benzyl-t-butylamine in 50 ml. of acetonitrile is refluxed for 3½ hours. The reaction mixture is cooled, 100 ml. of ether is added and filtered. The filtrate is evaporated and the residual oil is passed through an alumina column using a mixture of hexane and chloroform (4:6) as the eluent. The second component off the column is 4-benzyloxy-3-(1,2-diacetoxyethyl)-α-(N-benzyl-N-t-butylamino)acetophenone which is converted to its hydrochloride salt by ethereal hydrogen chloride.

The above prepared hydrochloride (2.0 g., 3.53 mm.) is dissolved in 100 ml. of ethanol and treated with 1.0 g. of sodium borohydride overnight at 24° C. The solvent is evaporated, the residue taken up in ethyl acetate, washed with water and dried. Evaporation of the ethyl acetate gives 4-benzyloxy-3-(1,2-dihydroxyethyl)-α-(N-benzyl-N-t-butylaminomethyl)-benzyl alcohol as an oil. The latter is converted to the hemifumarate salt by treating a solution of the free base in ethanol with 0.5 equivalent of fumaric acid; m.p. 147.5°–149° C.

A mixture of 800 mg. (1.78 mm.) of 4-benzyloxy-3-(1,2-dihydroxyethyl)-α-(N-benzyl-N-t-butylaminomethyl)-benzyl alcohol dissolved in 100 ml. of ethanol and 500 mg. of 10% palladium-on-carbon is hydrogenated on the Parr apparatus at 25° C. and 55 psi for 23 minutes. The reaction mixture is filtered and the filtrate is treated with a solution of 104 mg. (0.89 mm.) of fumaric acid in ethanol. The solvent is evaporated to give α-(t-butylaminomethyl)-3-(1,2-dihydroxyethyl)-4-hydroxybenzyl alcohol hemifumarate, m.p. 190°–191.5° c. (dec.).

Similarly, employing N-benzylisopropylamine in the reaction with α-bromo-4-benzyloxy-3-(1,2-diacetoxyethyl)-acetophenone and proceeding as described above yields the corresponding product 3-(1,2-dihydroxyethyl)-4-hydroxy-α-(isopropylaminomethyl)-benzyl alcohol.

EXAMPLE 2

Following the procedures outlined in Example 1, α-bromo-4-benzyloxy-3-(1,2-diacetoxyethyl)acetophenone is reacted with N-benzylcyclopentylamine to give 4-benzyloxy-3-(1,2-diacetoxyethyl)-α-(N-benzylcyclopentylamino)acetophenone hydrochloride. Similar reduction with sodium borohydride followed by hydrogenation over palladium-on-carbon gives α-(cyclopentylaminomethyl)-3-(1,2-dihydroxyethyl)-4-hydroxybenzyl alcohol.

Reacting α-bromo-4-benzyloxy-3-(1,2-diacetoxyethyl)acetophenone with N-benzyl-3,4-dimethoxyphenylisopropylamine followed by reduction, then hydrogenation yields the product 3-(1,2 -dihydroxyethyl)-α-[2-(3,4-dimethoxyphenyl)-1-methylethylaminomethyl]-4-hydroxybenzyl alcohol.

Similarly, employing N-benzylcyclopropylmethylamine in the above reaction followed by reduction and hydrogenation, there is obtained α-(cyclopropylmethylaminomethyl)-3-(1,2-dihydroxyethyl)-4-hydroxybenzyl alcohol.

EXAMPLE 3

Following the procedures of Example 1, condensation of 4-benzyloxy-α-bromo-3-(1,2-diacetoxyethyl)acetophenone with N-benzylphenylisopropylamine followed by reduction and hydrogenation yields 3-(1,2- dihydroxyethyl)-4-hydroxy-α-(2-phenyl-1-methylethylaminomethyl)-benzyl alcohol.

Similarly, reaction of 4-benzyloxy-α-bromo-3-(1,2-diacetoxyethyl)acetophenone with N-benzyl-3,4-dibenzyloxyphenylisopropylamine yields as the final product 3-(1,2-dihydroxyethyl)-α-[2-(3,4-dihydroxyphenyl)-1-methylethylaminomethyl]-4-hydroxybenzyl alcohol.

Reacting 4-benzyloxy-α-bromo-3-(1,2-diacetoxyethyl)-acetophenone with N-benzyl-4-benzyloxyphenylisopropylamine followed by reduction and hydrogenation gives 3-(1,2-dihydroxyethyl)-α-[2-(4-hydroxyphenyl)-1-methylethylaminomethyl]-4-hydroxybenzyl alcohol.

EXAMPLE 4

Following the procedure outlined in Example 1, 4-benzyloxy-α-bromo-3-(1,2-diacetoxyethyl)acetophenone is reacted with N-benzyl-2-(4-methoxyphenyl)-1,1-dimethylethylamine which followed by reduction and hydrogenation gives 3-(1,2-dihydroxyethyl)-α-[2-(4-methoxyphenyl)-1,1-dimethylethylaminomethyl]-4-hydroxybenzyl alcohol.

EXAMPLE 5

As described in Example 1, α-bromo-4-benzyloxy-3-(1,2-diacetoxyethyl)acetophenone is refluxed with N-benzyl-2-(3,4-methylenedioxyphenyl)-1-methylethylamine to give 4-benzyloxy-3-(1,2-diacetoxyethyl)-α-[N-benzyl-2-(3,4-methylenedioxyphenyl)-1-methylethylamino]acetophenone. Reduction with sodium borohydride followed by catalytic hydrogenation yields 3-(1,2-dihydroxyethyl)-4-hydroxy-α-[2-(3,4-methylenedioxyphenyl)-1-methylethylaminomethyl]-benzyl alcohol.

Similarly, reaction of the bromoacetophenone with N-benzyl-2-(4-benzyloxyphenyl)-1,1-dimethylethylamine to give 4-benzyloxy3-(1,2-diacetoxyethyl)-α-[N-benzyl-2-(4-benzyloxyphenyl)-1,1-dimethylethylamino]acetophenone followed by the above described reduction and catalytic hydrogenation yields the product 3-(1,2-dihydroxyethyl)-4-hydroxy-α-[2-(4-hydroxyphenyl)-1,1-dimethylethylaminomethyl]-benzyl alcohol.

EXAMPLE 6

| Ingredients | Mg./Tablet |
| --- | --- |
| α-(t-butylaminomethyl)-4-hydroxy-3-(1,2-dihydroxyethyl)-benzyl alcohol* | 10 |
| Starch, U.S.P. | 15 |
| Lactose, U.S.P. | 150 |
| Magnesium Stearate, U.S.P. | 1 |

*Added as the fumarate salt

A granulation of the above ingredients is compressed into tablets.

EXAMPLE 7

| Ingredients | Mg./Dose |
| --- | --- |
| α-(t-butylaminoethyl)-4-hydroxy-3-(1,2-dihydroxyethyl)-benzyl alcohol* | 0.125 |
| Alcohol, U.S.P. | 17 |
| Propellant (20% Freon 12/80% Freon 114 mixture) | 33 |

*Added as the fumarate salt

The above ingredients in an aerosol dispensing system with a metered valve furnishes the indicated amounts per dose.

EXAMPLE 8

A vigorously stirred solution of 10.0 g. (0.032 mol) of 2-[4-benzyloxy-3-(1,2-epoxyethyl)-phenyl]-2-methyl-1,3-dioxolane in 700 ml. of anhydrous methanol is treated with Dowex 50 (70 g., previously washed with 3N hydrochloric acid, water and methanol, then dried in vacuo at 95° C. for six hours). After five minutes the resin is removed by filtration and filtrate evaporated to dryness. The residue is dissolved in ethyl acetate and the solution is washed with 1N hydrochloric acid, water, dried and evaporated to dryness. The residue is triturated with ether to give 4-benzyloxy-3-(2-hydroxy-1-methoxyethyl)-acetophenone, m.p. 78°–80° C.

A solution of 10.6 g. (0.035 mol) of this acetophenone in 50 ml. of pyridine and 13 ml. of acetic anhydride is stirred at 25° C. for 18 hours. The solution is chilled, treated with 15 ml. of methanol, stirred for 20 minutes and poured into ethyl acetate. This solution is washed well with 5% hydrochloric acid, dried and evaporated to dryness. The residue is chromatographed to yield 4-benzyloxy-3-(2-acetoxy-1-methoxyethyl)-acetophenone, m.p. 67°–70° C.

To a solution of 6.6 g. (18.4 mmol) of the above prepared acetophenone in 100 ml. of chloroform is added a solution of bromine (0.975 ml, 19 mmol) in 20 ml. of chloroform. After 5 minutes one additional drop of bromine is added and stirring is continued for ten minutes. The mixture is washed with sodium bisulfite, water, dried and evaporated to dryness. The residue yields crystalline α-bromo-4-benzyloxy-3-(2-acetoxy-1-methoxyethyl)- acetophenone, m.p. 79°–80° C.

A mixture of 4.7 g. (11.16 mmol) of the α-bromo compound and 2.86 g. (17.5 mmol) of N-benzyl-t-butylamine in 35 ml. of acetonitrile is refluxed for five hours, then stirred at 25° C. for 18 hours. Ether (150 ml.) is added, the mixture is chilled, filtered and the filtrate evaporated to dryness. The residue is chromatographed on a silica gel column, eluting with ether-chloroform (1:9). The first fraction is evaporated to dryness to give α-(N-benzyl-N-t-butylamino)-4-benzyloxy-3-(2-acetoxy-1-methoxyethyl)-acetophenone.

A solution of 1.6 g. (3.18 mmol) of the acetophenone in 100 ml. of methanol is treated with 1.6 g. of sodium borohydride, stirred at 25° C. for 18 hours and evaporated to dryness. The residue is dissolved in ethyl acetate and the solution is washed with water, dried and evaporated to dryness. This residue is chromatographed to obtain α-(N-benzyl-N-t-butylaminomethyl)-4-benzyloxy-3-(2-hydroxy-1-methoxyethyl)-benzyl alcohol.

The benzyl alcohol (0.7 g., 1.5 mmol) in 150 ml. of ethanol is hydrogenated over 0.7 g. of 10% palladium-on-carbon at 50 psi for 25 minutes. The catalyst is filtered and the filtrate evaporated to give α-(t-butylaminomethyl)-4-hydroxy-3-(2-hydroxy-1-methoxyethyl)-benzyl alcohol; fumarate m.p. 230° C. (decomp.).

EXAMPLE 9

A solution of 10.0 g. (32.1 mmol) of 2-[4-benzyloxy-3-(1,2-epoxyethyl)-phenyl]-2-methyl-1,3-dioxolane and sodium methoxide (from 2.5 g. of sodium metal) in 500 ml. of methanol is refluxed for 5 hours and then stirred at 25° C. for 18 hours. The reaction mixture is evaporated to dryness and the reisude is dissolved in ether. The ether solution is washed with water, dried and evaporated to dryness to give a mixture of 3-(1-hydroxy-2-methoxyethyl)-phenyl and 3-(2-hydroxy-1-methoxyethyl)-phenyl dioxolanes. A solution of this mixture (10.0 g.) and 6.1 g. of freshly recrystallized trityl chloride in 25 ml. of pyridine is heated at 60°–70° C. for 2½ hours, then at 55°–60° C. for 18 hours. The solution is evaporated and the residue dissolved in a mixture of etherwater The ether is washed well with water, dried and evaporated. The residue is chromatographed on an alumina column to separate the trityl ether of the 3-(2-hydroxy-1-methoxyethyl)-phenyl dioxolane from the unreacted 3-(1-hydroxy-2-methoxyethyl)-phenyl dioxolane. The latter dissolved in tetrahydrofuran is treated with 1N hydrochloric acid and then extracted to yield 4-benzyloxy-3-(1-hydroxy-2-methoxyethyl)-acetophenone.

The acetophenone (4.3 g., 14.3 mmol) is acetylated in 60 ml. of pyridine with 5 ml. of acetic anhydride, with stirring at 25° C. for 18 hours. The reaction mixture is cooled, 10 ml. of methanol is added, and this mixture is stirred for 30 minutes, then poured into water and extracted with ether. The extract is washed well with 1N hydrochloric acid, water, dried and evaporated to dryness. The residue is passed through a silica gel column, eluting with ether. The first fraction is evaporated and this residue is recrystallized from chloroform-hexane to give 4-benzyloxy-3-(1-acetoxy-2-methoxyethyl)-acetophenone, m.p. 83°–84° C.

A solution of 2.9 g. (8.49 mmol) of the above prepared acetophenone in 200 ml. of chloroform is treated with 0.478 ml. (9.34 mmol) of bromine. After 30 minutes the reaction mixture is washed with water and 5% sodium bicarbonate solution, then dried and evaporated to dryness. The residue is recrystallized to give α-bromo-4-benzyloxy-3-(1-acetoxy-2-methoxyethyl)-acetophenone, m.p. 91°–93° C.

A mixture of 3.0 g. (7.13 mmol) of the bromo acetophenone and 2.21 g. (13.56 mmol) of N-benzyl-t-butylamine in 50 ml. of acetonitrile is refluxed for four hours. The solvent is evaporated and the residue is taken up in ether. The ether solution washed well with water, dried and treated with ethereal hydrogen chloride. The solvent is decanted and the gummy hydrochloride salt is dissolved in water. The aqueous solution is washed with ether, basified and extracted with ether. The extract is washed with water, dried and evaporated to leave α-(N-benzyl-N-t-butylamino)-4-benzyloxy-3-(1-acetoxy-2-methoxyethyl)-acetophenone.

To a solution of 2.2 g. (4.37 mmol) of this acetophenone in 70 ml. of ethanol is added 2.5 g. of sodium borohydride. After 18 hours at 25° C. the solvent is evaporated. The residue is dissolved in 50 ml. of methanol and 10 ml. of 20% potassium carbonate solution and this mixture is refluxed for 30 minutes. The methanol is evaporated and the mixture is extracted with ethyl acetate. The extract is washed with water, dried and evaporated to dryness. The residue is passed through a silica gel column, eluting with ether, and the first fraction is evaporated to give α-(N-benzyl-N-t-butylaminomethyl)-4-benzyloxy-3-(1-hydroxy-2-methoxyethyl)-benzyl alcohol.

A mixture of 1.0 g. (2.16 mmol) of the above benzyl alcohol and 1.0 g. of 10% palladium-on-carbon in 120 ml. of ethanol is hydrogenated at 50 psi for 10 minutes. The catalyst is filtered and the filtrate concentrated, then treated with ethereal hydrogen chloride to yield α-(t-butylaminomethyl)-4-hydroxy-3-(1-hydroxy-2-methoxyethyl)-benzyl alcohol hydrochloride, m.p. 194°–195° C.

What is claimed is:

1. A chemical compound of the formula:

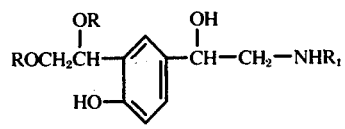

or a pharmaceutically acceptable acid addition salt of said compound, wherein:

R is hydrogen or methyl, with both R's not being methyl at the same time;

$R_1$ is branched chain lower alkyl of from 3 to 5 carbon atoms, cycloalkyl or cycloalkylmethyl, the cycloalkyl moiety having from 3 to 6 carbon atoms, or

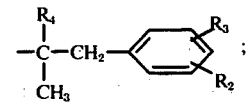

$R_2$ and $R_3$ are hydrogen, hydroxy, methoxy or, taken together in adjacent positions, methylenedioxy; and $R_4$ is hydrogen or methyl.

2. The chemical compound according to claim 1 in which R is hydrogen.

3. A chemical compound according to claim 2 in which $R_1$ is t-butyl, being the compound α-(t-butylaminomethyl)-3-(1,2-dihydroxyethyl)-4-hydroxybenzyl alcohol.

4. The chemical compound according to claim 2 in which $R_1$ is cyclopentyl, being the compound α-(cyclopentylaminomethyl)-3-(1,2-dihydroxyethyl)-4-hydroxy-benzyl alcohol.

5. The chemical compound according to claim 2 in which $R_1$ is isopropyl, being the compound 3-(1,2-dihyroxyethyl)-4-hydroxy-α-isopropylaminomethyl-benzyl alcohol.

6. The chemical compound according to claim 2 in which $R_1$ is 2-(3,4-methylenedioxyphenyl)-1-methylethyl, being the compound 3-(1,2-dihydroxyethyl)-4-hydroxy-α-[2-(3,4-methylenedioxyphenyl)-1-methylethylaminomethyl]-benzyl alcohol.

7. The chemical compound according to claim 2 in which $R_1$ is 2-(4-hydroxyphenyl)-1,1-dimethylethyl, being the compound 3-(1,2-dihydroxyethyl)-4-hydroxy-α-[2-(4-hydroxyphenyl)-1,1-dimethylethylaminomethyl]-benzyl alcohol.

8. A chemical compound of the formula:

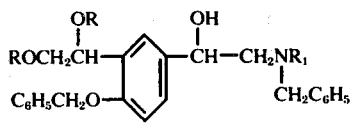

wherein:
R is hydrogen or methyl, with both R's not being methyl at the same time;
$R_1$ is branched chain lower alkyl of from 3 to 5 carbon atoms, cycloalkyl or cycloalkylmethyl, the cycloalkyl moiety having from 3 to 6 carbon atoms, or

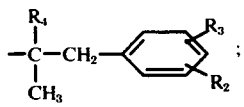

$R_2$ and $R_3$ are hydrogen, hydroxy, methoxy or, taken together in adjacent positions, methylenedioxy; and
$R_4$ is hydrogen or methyl.

9. The chemical compound according to claim 8 in which R is hydrogen.

10. A pharmaceutical composition having β-adrenergic stimulant activity in dosage unit form comprising a pharmaceutical carrier and an effective amount of a chemical compound of the formula:

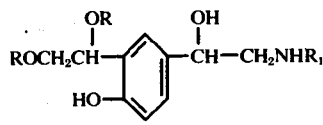

or a pharmaceutically acceptable acid addition salt of said compound, wherein:
R is hydrogen or methyl, with both R's not being methyl at the same time;
$R_1$ is branched chain lower alkyl of from 3 to 5 carbon atoms, cycloalkyl or cycloalkylmethyl, the cycloalkyl moiety having from 3 to 6 carbon atoms, or

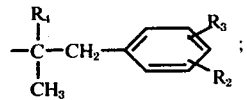

$R_2$ and $R_3$ are hydrogen, hydroxy, methoxy, or, taken together in adjacent positions, methylenedioxy; and
$R_4$ is hyrogen or methyl.

11. The pharmaceutical composition according to claim 10 in which R is hydrogen.

12. The pharmaceutical composition according to claim 11 in which $R_1$ is t-butyl, the active ingredient being the compound α-(t-butylaminomethyl)-3-(1,2-dihydroxyethyl)-4-hydroxybenzyl alcohol.

13. A method of producing β-adrenergic stimulant activity which comprises administering internally to animals in need thereof an amount sufficient to produce said activity of a chemical compound of the formula:

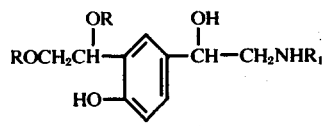

or a pharmaceutically acceptable acid addition salt of said compound, wherein:
R is hydrogen or methyl, with both R's not being methyl at the same time;
$R_1$ is branched chain lower alkyl of from 3 to 5 carbon atoms, cycloalkyl or cycloalkylmethyl, the cycloalkyl moiety having from 3 to 6 carbon atoms, or

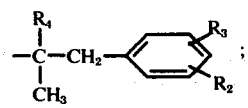

$R_2$ and $R_3$ are hydrogen, hydroxy, methoxy, or, taken together in adjacent position, methylenedioxy; and
$R_4$ is hydrogen or methyl.

14. The method according to claim 13 in which R is hydrogen.

15. The method according to claim 14 in which $R_1$ is t-butyl, the active ingredient being the compound α-(t-butylaminomethyl)-3-(1,2-dihydroxyethyl)-4-hydroxybenzyl alcohol.

16. The chemical compound according to claim 1 in which one of the R's is hydrogen and the other is methyl.

17. The chemical compound according to claim 16 in which $R_1$ is t-butyl.

18. The chemical compound according to claim 17 being the compound α-(t-butylaminomethyl)-4-hydroxy-3-(2-hydroxy-1-methoxyethyl)-benzyl alcohol.

19. The chemical compound according to claim 17 being the compound α-(t-butylaminomethyl)-4-hydroxy-3-(1-hydroxy-2-methoxyethyl)-benzyl alcohol.

* * * * *